United States Patent
Wei et al.

(10) Patent No.: US 7,376,213 B1
(45) Date of Patent: May 20, 2008

(54) CT IMAGE RECONSTRUCTION THROUGH EMPLOYMENT OF FUNCTION THAT DESCRIBES INTERPRETED MOVEMENT OF SOURCE AROUND PARTICULAR POINT OF OBJECT

(75) Inventors: Yuchuan Wei, Iowa City, IA (US); Jiang Hsieh, Brookfield, WI (US); Ge Wang, Iowa City, IA (US)

(73) Assignees: General Electric Company, Schenectady, NY (US); University of Iowa Research Foundation, Iowa City, IA (US)

( * ) Notice: Subject to any disclaimer, the term of this patent is extended or adjusted under 35 U.S.C. 154(b) by 164 days.

(21) Appl. No.: 11/276,301

(22) Filed: Feb. 23, 2006

(51) Int. Cl.
*G01N 23/00* (2006.01)
(52) U.S. Cl. .................. 378/4; 378/8; 378/39
(58) Field of Classification Search .............. 378/4, 378/8, 38, 39, 901
See application file for complete search history.

(56) References Cited

U.S. PATENT DOCUMENTS

| | | | |
|---|---|---|---|
| 3,908,126 A * | 9/1975 | Hudson et al. ............... 378/39 |
| 4,034,225 A * | 7/1977 | Hudson et al. ............... 378/39 |
| 4,093,863 A * | 6/1978 | Zacher, Jr. .................... 378/4 |
| 5,214,686 A * | 5/1993 | Webber ........................ 378/38 |
| 5,301,108 A | 4/1994 | Hsieh |
| 6,236,705 B1 * | 5/2001 | Stergiopoulos et al. ........ 378/8 |
| 2002/0025017 A1 * | 2/2002 | Stergiopoulos et al. ........ 378/8 |
| 2002/0085681 A1 * | 7/2002 | Jensen ........................ 378/197 |
| 2005/0175144 A1 | 8/2005 | Hsieh |

FOREIGN PATENT DOCUMENTS

JP         09164133 A  *  6/1997

OTHER PUBLICATIONS

Wang et al., A General Cone-Beam Reconstruction Algorithm, IEEE Transactions on Medical Imaging, vol. 12, No. 3, Sep. 1993, pp. 486-496.*
Michael Defrise et al., "A Combination of Rebinning and Exact Reconstruction Algorithms for Helical Cone-Beam CT,".
"Closed Curve" from MathWorld.

(Continued)

*Primary Examiner*—Courtney Thomas
*Assistant Examiner*—Alexander H Taningco
(74) *Attorney, Agent, or Firm*—Ziolkowaki Patent Solutions Group, SC

(57) ABSTRACT

A CT system in an example comprises an x-ray source, a detector, a data acquisition system (DAS), and a computer. The x-ray source emits a beam of x-rays toward an object to be imaged. The detector receives x-rays emitted by the x-ray source. The DAS is operably connected to the detector. The computer is operably connected to the DAS. The computer is programmed to reconstruct a CT image of the object to comprise a plurality of CT images, of a respective plurality of points of the object, through employment of a function that describes how many times a trajectory curve, of an interpretation of relative movement between the x-ray source and the object as that of the x-ray source, goes around each of the plurality of points of the object.

20 Claims, 11 Drawing Sheets

OTHER PUBLICATIONS

Eli Benveniste, "Comparison of Two-Dimensional Rebinning Algorithms for Image Reconstruction from Projections,".
Enrique Solano, "Concatenation and Rebinning of IUE High Resolution Spectra," pp. 1-8.
CT Rays vs. Image Reconstruction.
CT Reconstruction.
Michael Defrise et al., "Fourier Rebinning of Time-of-Flight PET Data," Phys. Med. Biol. 50 (2005) 2749-2763.
Yuchuan Wei et al., "General Formula for Fan-Beam Computed Tomography," PRL 95, 258102 (2005).
"Locus" from MathWorld.
Yunnan Wu et al., "Smart Rebinning for the Compression of Concentric Mosaic," IEEE Transactions on Multimedia, vol. 4, No. 3, Sep. 2002.
"Tomographic Image Reconstruction," pp. 1-10.

\* cited by examiner

CT IMAGE RECONSTRUCTION THROUGH EMPLOYMENT OF FUNCTION THAT DESCRIBES INTERPRETED MOVEMENT OF SOURCE AROUND PARTICULAR POINT OF OBJECT

BACKGROUND OF THE INVENTION

The present invention relates generally to diagnostic imaging and, more particularly, to image reconstruction.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

To acquire CT images, generally, one of two projection geometries is used; either a parallel beam geometry or a fan beam geometry. With parallel beam geometry, all x-rays in a projection are parallel to one another. With fan beam geometry, the x-rays at a given projection angle diverge resulting in a fan-like appearance. Most modern CT scanners use fan beam geometry in the acquisition and reconstruction of CT images. Notwithstanding the advantages of fan beam geometry relative to parallel beam geometry, some constraints are placed thereon.

Specifically, fan beam reconstruction was first studied and modeled in the circular scanning case, and later extended to the case of non-circular scanning loci with some constraints. In this regard, conventional fan beam reconstructions are generally based on the Radon formula or the parallel beam reconstruction formula, and completed via the coordinate transformation from parallel beam to fan beam geometry. As a result, conventional fan beam reconstruction techniques are not well-suited for acquiring data from non-still objects, such as during head scans.

For example, a patient having a head CT may be unable to hold the head still and steady during the CT scanning. The movement of the head may result from the patient being young, old, severely injured, or other reasons. Head motion of the patient occurs more often in head perfusion CT. In this technique to measure cerebral blood flow, the same slice of the head is continuously scanned and circumscribed. A specified slice of the brain may be scanned for forty to fifty seconds continuously. A contrast material is injected and the rise and fall of the contrast is monitored within the blood vessels and all the other surrounding tissue. A perfusion map is built to measure several key physiological parameters for the brain such as the mean transit time and blood volume. Since the head is supposed to be an object fixed in space, any movement during data acquisition can negatively affect the CT images acquired therefrom.

Therefore, it would be desirable to design an apparatus and method that enables CT imaging for moving objects with a circular source locus, and CT imaging for a still object with a complicated source locus.

BRIEF DESCRIPTION OF THE INVENTION

The invention in an implementation encompasses a CT system. The CT system comprises an x-ray source, a detector, a data acquisition system (DAS), and a computer. The x-ray source emits a beam of x-rays toward an object to be imaged. The detector receives x-rays emitted by the x-ray source. The DAS is operably connected to the detector. The computer is programmed to reconstruct a CT image of the object to comprise a plurality of CT images, of a respective plurality of points of the object, through employment of a function that describes how many times a trajectory curve, of an interpretation of relative movement between the x-ray source and the object as that of the x-ray source, goes around each of the plurality of points of the object.

Another implementation of the invention encompasses a method. Relative movement between a high frequency electromagnetic energy projection source and a target object is interpreted as interpreted movement of the high frequency electromagnetic energy projection source relative to a coordinate system fixed with respect to the target object for an interpretation of CT image data of the target object. A CT image of the target object is reconstructed through employment of a function that describes how many times the interpreted movement of the high frequency electromagnetic energy projection source goes around a particular point of the target object.

A further implementation of the invention encompasses a method for CT imaging with a complicated scanning trajectory. Filtering projection data employs Ram-Lak filter or a variant of the Ram-Lak filter. The projection data correspond to the complicated scanning trajectory. The projection data are multiplied by increments relative to a view angle and focus distance. The projection data is backprojected to form an image through employment of a turn number function.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems. Exemplary implementations comprise one or more of a "third generation" CT scanner, "fourth generation" CT scanner, and/or other type of CT system.

Figure 1:
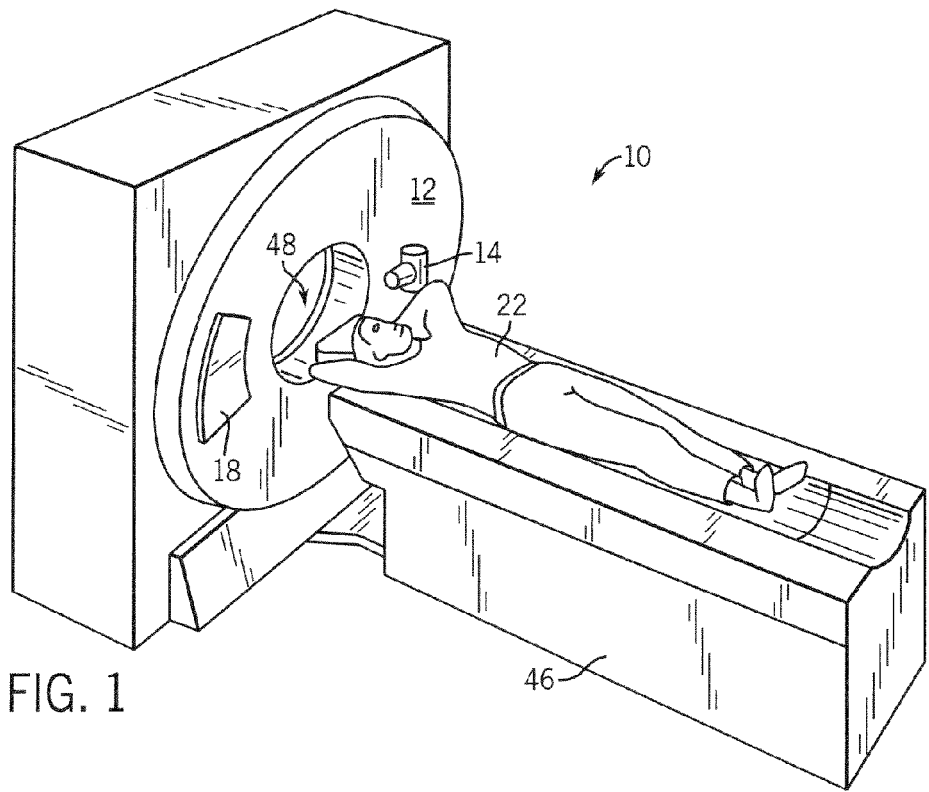
FIG. 1 is a pictorial view of a CT imaging system.
Figure 2:
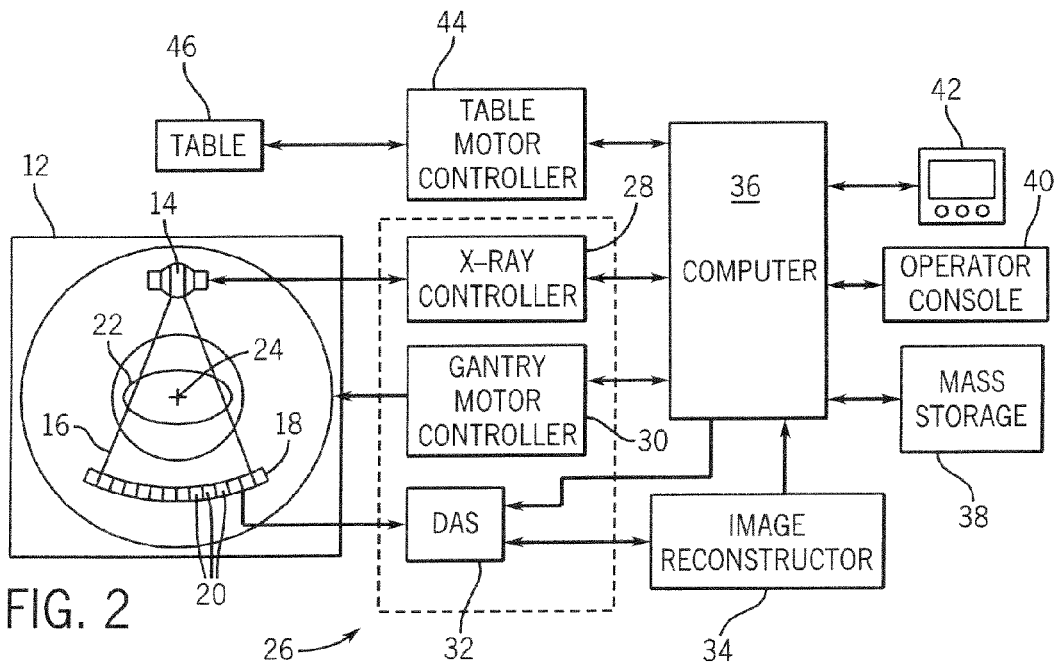
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from the DAS 32 and performs high speed reconstruction. The image reconstructor 34 in an example comprises a computer that interprets information from the DAS 32 and performs reconstruction of an object to be imaged. The image reconstructor 34 comprises a recordable data storage medium. The reconstructed image is applied as an input to a computer 36 which stores the image in a mass storage device 38. The mass storage device 38 comprises a recordable data storage medium, as described herein.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Presented herein is a new fan-beam reconstruction formula. The fan-beam reconstruction formula is implemented in software that is part of the reconstruction engine, for example, the image reconstructor 34. The reconstruction engine of the image reconstructor 34 in an example performs the image formation and reconstruction. For illustrative purposes, an exemplary description is developed herein from arbitrary closed scanning curves to a scanning locus that is not necessarily closed. Differences exist between the following formulation and an exemplary previous formulation. A starting point of the exemplary deduction below is a property of the ramp filter, instead of the Radon formula or the parallel-beam reconstruction formula. There is a removal or cancellation of an exemplary previous assumption or constraint that the function to be recovered must take zero value outside the scanning locus. There is avoidance of the variable change between parallel and fan beam geometry. The locus needs to be continuous rather than differentiable.

Exemplary applications comprise CT imaging of moving objects and image reconstruction with flexibility in the source trajectory. The source trajectory comprises a general nature. In an example, the fan-beam reconstruction formula combats motion and provides a convenience of using the object as the reference coordinate. In another example, the fan-beam reconstruction formula applies to cases where the object is stationary while the source moves about the object in a very flexible and/or unusual fashion.

In an exemplary head CT, the patient may have difficulty remaining still and have a tendency to move around during forty to fifty seconds of acquisition time. The fan-beam reconstruction formula takes into consideration movement of the patient and allows reconstruction of an image after the patient has moved around during the imaging. Thus the patient need not be scanned again.

Figure 3:
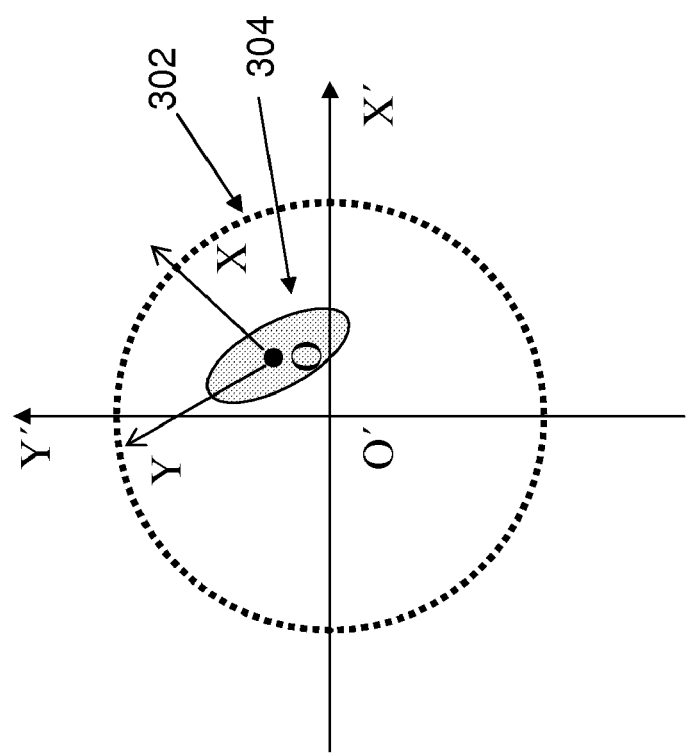
FIG. 3 represents a prior art coordinate system for an exemplary previous approach to head perfusion CT with an orientation external to the patient.

Turning to FIG. 3, an X'-Y' coordinate system for an exemplary previous approach to head perfusion CT comprises an orientation external to the patient 22. The x-ray source 14 comprises a trajectory 302 as the x-ray source 14 moves or rotates about an object to be imaged or target object 304, for example, the head of the patient 22. The origin O' of the X'-Y' coordinate system locates at the center of the gantry opening 48. As the x-ray source 14 and the detector array 18 rotate about the patient, the x-ray source 14 follows the circle of the trajectory 302. The target object 304 is the target of the CT scan.

Figure 4:
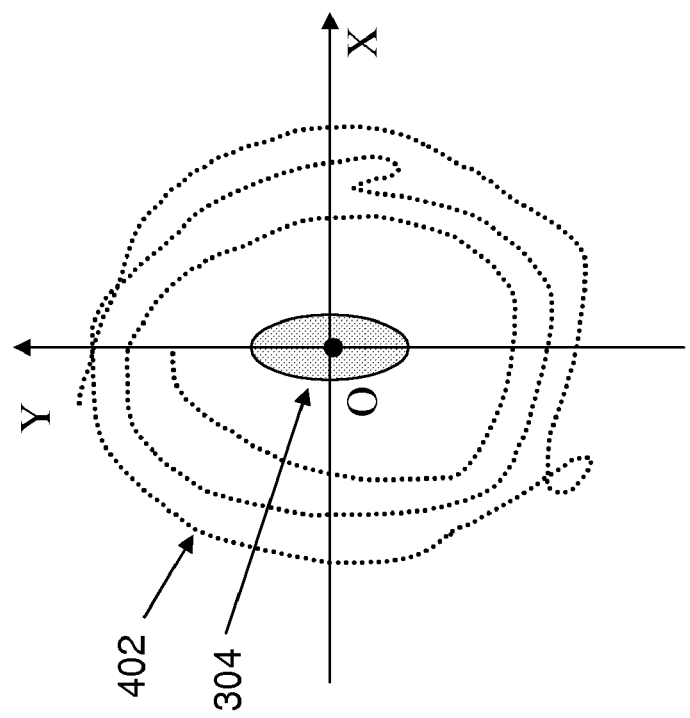
FIG. 4 illustrates an object as a reference coordinate for a scan by a high frequency electromagnetic energy projection source and a resultant interpreted trajectory of the high frequency electromagnetic energy projection source.

Turning to FIG. 4, the target object 304 comprises a reference coordinate. For example, the frontal lobe of the brain as the target object 304 comprises the origin O of the X-Y coordinate system. As the patient 22 moves in the X'-Y' coordinate system then the source 14 is considered to move in the opposite direction of the actual movement of the patient 22. Trajectory 402 of the x-ray source 14 as interpreted in the X-Y coordinate system becomes an odd shape. An exemplary previous approach to reconstruction algorithms of a non-circular trajectory placed limitations on the type of trajectory that was possible, and if certain conditions were unsatisfied the derivation would not work. The new derivation presented herein allows for a much more general trajectory shape for the x-ray source 14. For example, the trajectory 402 of the x-ray source 14 in some places goes back and forth and in some places loops around.

The gantry 12 in an example operates the same as in an exemplary previous approach. For example, the gantry 12 operates the same when the x-ray source 14 comprises the trajectory 302 as well as when the x-ray source 14 comprises the trajectory 402. An exemplary difference is motion of the patient 22. An exemplary previous reconstruction algorithm could not tolerate certain motion patterns by the patient 22. The new algorithm allows reconstruction of the image even when the patient 22 moves in a complex pattern. This formula is useful for CT imaging of the target object 304 with in-plane motion and has been numerically simulated using the Shepp-Logan phantom, as described herein. For example, CT reconstruction is provided in the event of head motion by the patient 22 where an exemplary previous approach would simply fail to provide a quality image, fails to provide an accurate representation of the target object 304, and/or fails to return a result that the reconstruction algorithm does not apply because a condition is unmet. In another example, the new algorithm allows reconstruction of the image even when the x-ray source 14 moves in a complex pattern. CT reconstruction is provided in other motion cases for the x-ray source 14.

The trajectory 402 of the x-ray source 14 comprises a conversion where the x-ray source 14 is viewed as having changes in radius and direction and accounts for one or more of actual movement of the x-ray source 14 and/or actual movement of the target object 304. The trajectory 402 represents a view or interpretation from the X-Y coordinate system fixed on the target object 304, of how the x-ray source 14 moves. From this view, the target object 304 always remains stationary and the x-ray source 14 has changes in the trajectory 402. In an example, this is a more convenient way to analyze the problem.

The trajectory 402 of the x-ray source 14 in an example comprises an arbitrary trajectory. Where the target object 304 comprises a head of the patient 22 with an in-plane motion, the analysis of circular fan-beam scans with respect to the head of the patient 22 in an example is equivalent to the analysis of complicated non-circular scans with respect to a stationary head. Information about possible motion of the head of the patient 22 can be extracted accurately, for example, by using a 3D camera or analyzing the projection data.

Now is presented an illustrative derivation of an exemplary fan-beam reconstruction formula for general closed locus, for explanatory purposes. The ramp filter is provided in exemplary equation (1):

$$h(t) = \int_{-\infty}^{+\infty} |\omega| \exp(i 2\pi \omega t) d\omega = -\frac{1}{2\pi^2 t^2} \quad (1)$$

and has a property provided in exemplary equation (2):

$$\frac{1}{2} \int_0^{2\pi} h(x \cos\tilde{\beta} + y \sin\tilde{\beta}) d\tilde{\beta} = \delta(\vec{r}), \quad (2)$$

where $\vec{r} = (x, y)$ is a point in a general two dimensional plane XOY.

Based on exemplary equation (2), we have the following further relations of exemplary equations (3):

$$\frac{1}{2} \int_0^{2n\pi} h(x \cos\tilde{\beta} + y \sin\tilde{\beta}) d\tilde{\beta} = n\delta(\vec{r}), \quad (3)$$

$$\frac{1}{2} \int_0^{2n\pi} h((x_2 - x_1) \cos\tilde{\beta} + (y_2 - y_1) \sin\tilde{\beta}) d\tilde{\beta} = n\delta(\vec{r}_2 - \vec{r}_1),$$

with n= . . . , −2,−1,0,1,2, . . . . Here $\vec{r}_1 = (x_1, y_1)$ and $\vec{r}_2 = (x_2, y_2)$ are two points in the plane.

Figure 5:
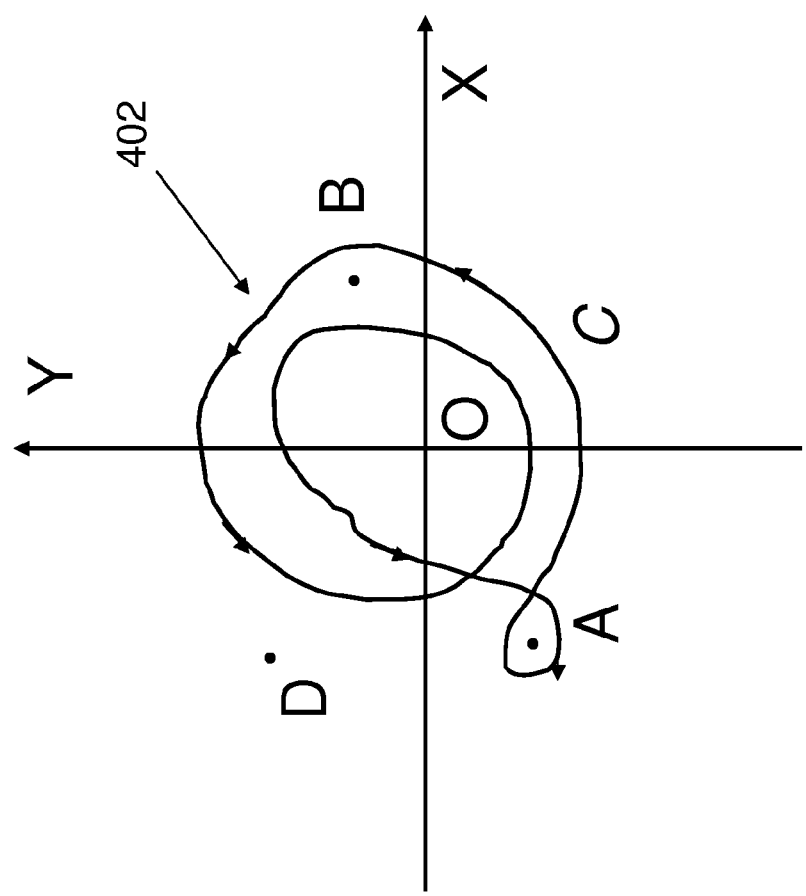
FIG. 5 illustrates an exemplary curve of trajectory of a high frequency electromagnetic energy projection source in a plane for employment with an exemplary function that describes how many times interpreted movement of the high frequency electromagnetic energy projection source goes around a particular point of an object.

Turning to FIG. 5, an exemplary oriented closed curve C in a plane OXY is employable with an exemplary function that describes how many times interpreted movement of a high frequency electromagnetic energy projection source goes around a particular point of the target object 304. The exemplary function in an example comprises a turn number function defined below in exemplary equation (4). Curve C in an example comprises a continuous closed curve in the OXY plane. Curve C represents the trajectory 402 of a high frequency electromagnetic energy projection source. For example, curve C comprises the trajectory 402 of the x-ray source 14 and is interpreted from the X-Y coordinate system fixed on the target object 304.

Exemplary equation (4) defines the turn number function:

$$N(\vec{r}) = n \quad (4)$$

to describe how many times the curve C goes around a given point $\vec{r}$ counterclockwise. For exemplary points O, A, B, and D on the target object 304 exemplary equations (5) provide:

$$N(O)=2, N(A)=-1, N(B)=1, N(D)=0. \quad (5)$$

The turn number function N is undefined for points on the curve C which form only a point set with measure 0. Additional discussion of exemplary equations (5) and FIG. 5 is presented herein in connection with exemplary equation (13).

Figure 6:
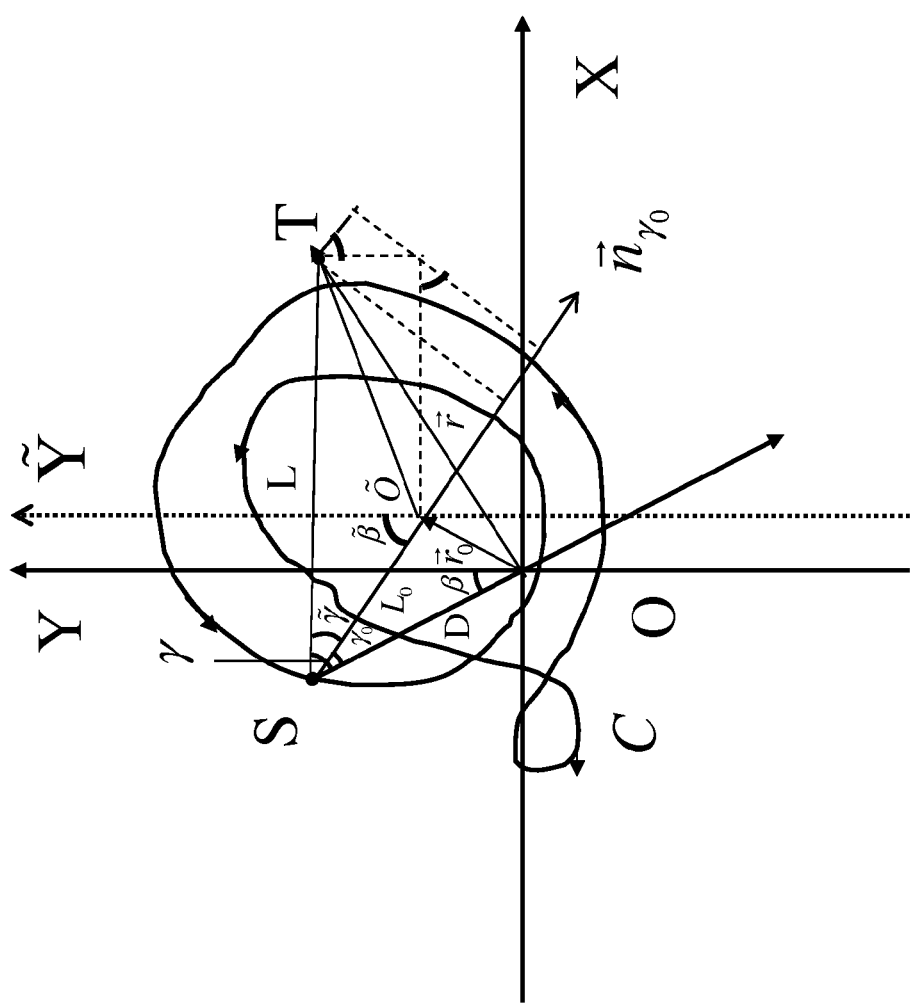
FIG. 6 illustrates exemplary geometry of fan-beam reconstruction for an exemplary curve of trajectory of a high frequency electromagnetic energy projection source.

Turning to FIG. 6, exemplary geometry of fan-beam reconstruction for curve C of the trajectory 402 of a high frequency electromagnetic energy projection source is represented.

Curve C in an example comprises a closed curve in the OXY plane and S is a point on the curve C. $\tilde{O}$ is a point in the plane but not on the curve C, with a position vector $\vec{r}_0 = (x_0, y_0)$. $\tilde{O}\tilde{Y}$ is parallel to the axis OY with $\angle \tilde{Y}\tilde{O}S = \tilde{\beta}$.

T is a point in the plane with a position vector $\vec{r} = (x, y)$. Based on exemplary equation (3), one obtains exemplary equation (6):

$$\frac{1}{2}\int_C h((x-x_0)\cos\tilde{\beta} + (y-y_0)\sin\tilde{\beta})d\tilde{\beta} = \frac{1}{2}\int_0^{2\pi N(\vec{r}_0)} h((x-x_0)\cos\tilde{\beta} + (y-y_0)\sin\tilde{\beta})d\tilde{\beta} = N(\vec{r}_0)\delta(\vec{r}-\vec{r}_0). \qquad (6)$$

Denoting $ST = L$ and $\angle \tilde{O}ST = \tilde{\gamma}$ results in exemplary equation (7):

$$(x-x_0)\cos\tilde{\beta} + (y-y_0)\sin\tilde{\beta} = L\sin\tilde{\gamma} \qquad (7)$$

Therefore, exemplary equation (3) becomes exemplary equation (8):

$$\frac{1}{2}\int_C h(L\sin\tilde{\gamma})d\tilde{\beta} = N(\vec{r}_0)\delta(\vec{r}-\vec{r}_0). \qquad (8)$$

Furthermore, denoting $$\angle OS\tilde{O} = \gamma_0, \ S\tilde{O} = L_0, \ SO = D, \ \angle OST = \gamma,$$

results in exemplary equation (9):

$$d\tilde{\beta} = \frac{1}{L_0}(D\cos\gamma_0 d\beta - \sin\gamma_0 dD), \qquad (9)$$

Figure 7:
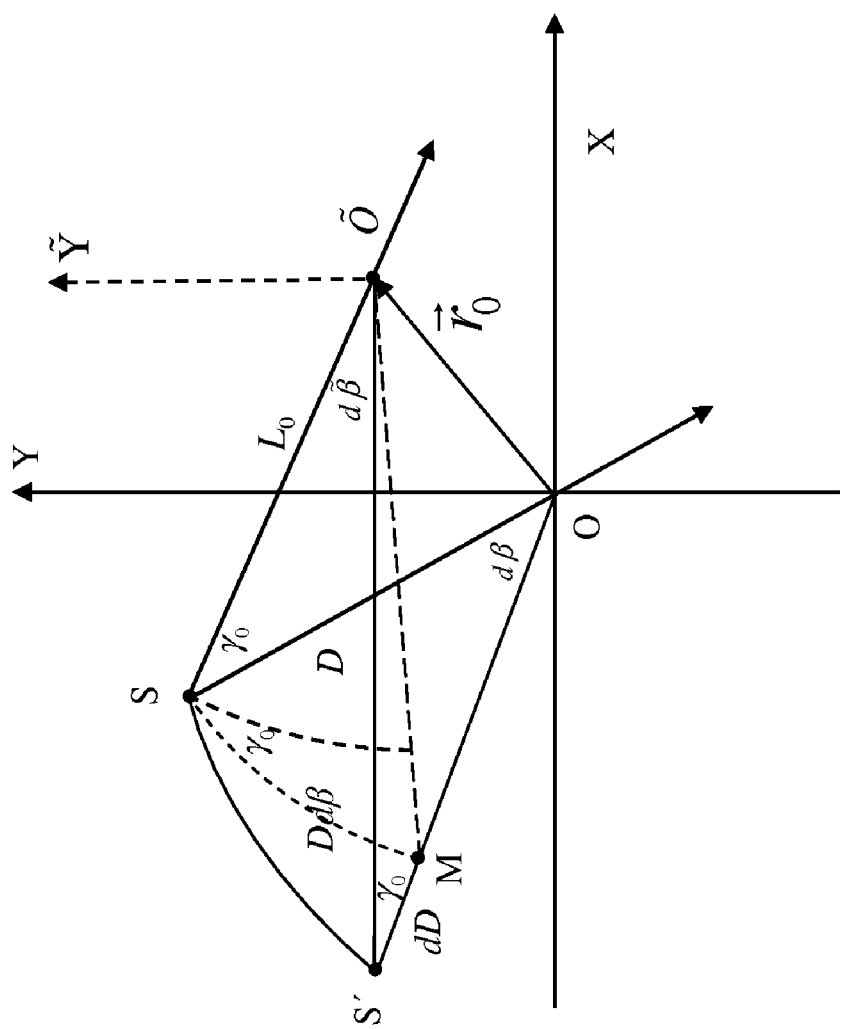
FIG. 7 illustrates an exemplary relationship in derivation of an exemplary fan-beam reconstruction formula.

The relationship between $d\beta$ and $d\tilde{\beta}$ of exemplary equation (9) is illustrated in FIG. 7.

Referring to FIG. 7, SS' comprises a relatively small arc. From S to S' the position parameters (D, $\beta$) change to (D+dD, $\beta$+d$\beta$). This process can be divided into two steps: SM and MS' with OM=OS=D.

Employing exemplary equation (9) allows exemplary equation (8) to be rewritten as:

$$\frac{1}{2}\int_C h(L\sin(\gamma-\gamma_0))\frac{1}{L_0}(D\cos\gamma_0 d\beta - \sin\gamma_0 dD) = N(\vec{r}_0)\delta(\vec{r}-\vec{r}_0). \qquad (10)$$

Applying exemplary equation (10) to a 2-Dimensional test function $\Psi(\vec{r}_0)$, one obtain exemplary equations (11) and (12):

$$(N(\vec{r}_0)\delta(\vec{r}-\vec{r}_0), \Psi(\vec{r}_0)) = \int\int_{R^2} N(\vec{r}_0)\delta(\vec{r}-\vec{r}_0)\Psi(\vec{r}_0)d\vec{r}_0 = N(\vec{r})\Psi(\vec{r}), \qquad (11)$$

and $$\left(\frac{1}{2}\int_C h(L\sin(\gamma-\gamma_0))\frac{1}{L_0}(D\cos\gamma_0 d\beta - \sin\gamma_0 dD), \Psi(\vec{r}_0)\right) = \qquad (12)$$

$$\int\int_{R^2} \frac{1}{2}\int_C h(L\sin(\gamma-\gamma_0))\frac{1}{L_0}(D\cos\gamma_0 d\beta - \sin\gamma_0 dD)\Psi(\vec{r}_0)d\vec{r}_0 =$$

$$\frac{1}{2}\int_C\int\int_{R^2} \Psi(\vec{r}_0)h(L\sin(\gamma-\gamma_0))\frac{1}{L_0}(D\cos\gamma_0 d\vec{r}_0 d\beta -$$

$$\sin\gamma_0 d\vec{r}_0 dD) = \frac{1}{2}\int_C\int_{-\pi}^{\pi}\int_0^{\infty} \Psi(\vec{r}_0)dL_0 h(L\sin(\gamma -$$

$$\gamma_0))(D\cos\gamma_0 d\gamma_0 d\beta - \sin\gamma_0 d\gamma_0 dD) =$$

$$\frac{1}{2}\int_C\int_{-\pi}^{\pi} R(\beta,\gamma_0)h(L\sin(\gamma-\gamma_0))(D\cos\gamma_0 d\gamma_0 d\beta - \sin\gamma_0 d\gamma_0 dD).$$

A result in an implementation is exemplary equation (13) as a new fan-beam reconstruction formula for a general closed curve:

$$\frac{1}{2}\int_C\int_{-\pi}^{\pi} R(\beta,\gamma_0)h(L\sin(\gamma-\gamma_0))(D\cos\gamma_0 d\gamma_0 d\beta - \sin\gamma_0 d\gamma_0 dD) = \qquad (13)$$

$$N(\vec{r})\Psi(\vec{r}),$$

where exemplary equation (14):

$$R(\beta,\gamma_0) = \int_0^{\infty} \Psi(\vec{r}_0)dL_0 = \int_0^{\infty} \Psi(\vec{OS} + L_0\vec{n}_{\gamma_0})dL_0 \qquad (14)$$

is referred to as the projection at the view angle $\beta$, and the fan angle $\gamma_0$. $\vec{n}_{\gamma 0}$ is the norm direction associated with $\gamma_0$.

The turn number function N from exemplary equations (4) and (13) in an example represents an advance. The employment of the turn number function N from exemplary equation (13) represents an exemplary advancement in image reconstruction. The turn number function N looks outward from a particular point of interest on the target object 304 and counts in the curve C of the trajectory 402 of the x-ray source 14, the number of clockwise and counter-clockwise turns about a particular point of interest on the target object 304. The turn number function N in an example yields a net number of times that the curve C of the trajectory 402 of the x-ray source 14, goes around about a particular point on the target object 304 in the counter-clockwise direction, as represented above in exemplary equations (5) for exemplary points O, A, B, C, and D on the target object 304 in FIG. 5.

Referring again to FIG. 5 and exemplary equations (5), the turn number function N for the exemplary point O on the target object 304 is 2 because the curve C goes around the exemplary point O twice in the counter-clockwise direction. The turn number function N for the exemplary point A on the target object 304 is −1 because the curve C goes around the exemplary point A once in the clockwise direction. The turn number function N for the exemplary point B on the target object 304 is 1 because the curve C goes around the exemplary point B once in the counter-clockwise direction. The turn number function N for the exemplary point D on the target object 304 is 0 because the curve C does not go around the exemplary point D.

The counter-clockwise direction was selected as a reference direction in the exemplary derivation of the reconstruction formula of exemplary equation (13). Another exemplary derivation of the reconstruction formula could use the clockwise direction as the reference direction. The reconstruction formula of exemplary equation (13) is linked to the turn number function N presented in exemplary equation (4). The turn number function N could be defined as the number of times an oriented closed curve loops around a point on the target object 304. A curve that loops around a given point on the target object 304 clockwise as well as counter-clockwise in an example has positive and negative component values for the turn number function N which tend to cancel each other out.

For example, in reconstructing the image of the exemplary point O, the contribution in the trajectory 402 of the x-ray source 14 from the part of the curve C that comprises the tight loop around exemplary point A would be canceled automatically since a subpart of the tight loop is clockwise with respect to the exemplary point O and the remainder of the tight loop is counter-clockwise with respect to the exemplary point O. An exemplary previous approach would lack an ability to treat and/or handle the trajectory 402 of the x-ray source 14 in the curve C, the tight loop around exemplary point A in the reconstruction of the image of the exemplary point O of the target object 304. In the reconstruction formula of exemplary equation (13) applied to the reconstruction of the image of exemplary point O of the target object 304, the contributions will advantageously cancel each other out for all the source trajectories in the part of the curve C that comprises the tight loop about exemplary point A.

The value of the turn number function N for a given point on the target object 304 is significant in the reconstruction formula of exemplary equation (13). The reconstruction formula of exemplary equation (13) cannot create an image for a point on the target object 304 whose turn number function N yields the value of zero. The turn number function N applied to the exemplary point D on the target object 304 does yield the value of zero and provides notice that the reconstruction formula of exemplary equation (13) cannot create an image for the exemplary point D on the target object 304.

Given the trajectory 402 of the x-ray source 14, the reconstruction formula of exemplary equation (13) determines which points on the target object 304 can and cannot have their image reconstructed by the image reconstructor 34. Further, the non-zero values provided by the turn number function N for particular points on the target object 304 give information on how the image reconstructor 34 is to perform the reconstruction of the image at each of those points on the target object 304. For every point on the target object 304, the reconstruction formula of exemplary equation (13) looks at how many times the trajectory 402 of the x-ray source 14 in the curve C goes around the point.

Figure 8:
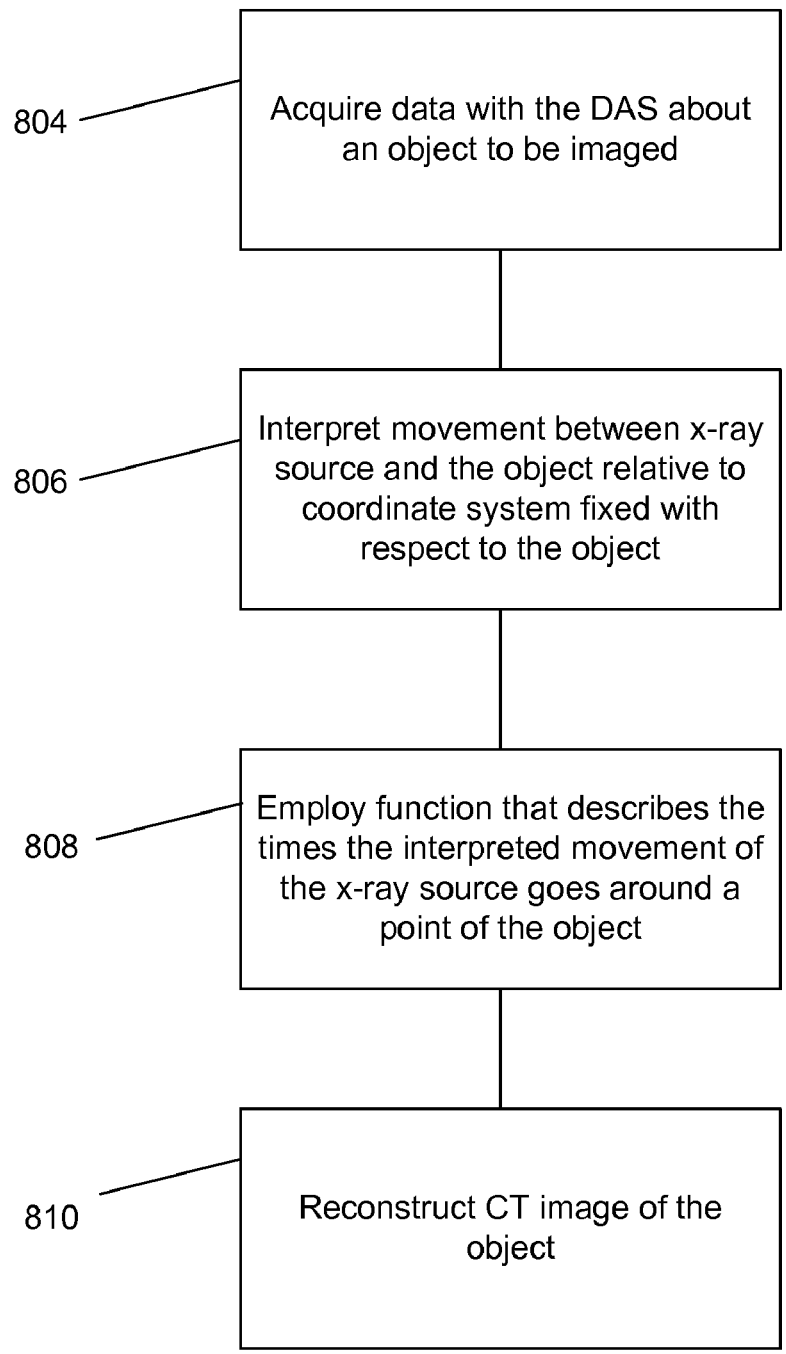
FIG. 8 is a representation of an exemplary logic flow for CT image reconstruction.

Turning to FIG. 8, in exemplary logic flow 802 at Step 804, the DAS 32 acquires data about the object 304. At Step 806, the image reconstructor 34 interprets movement between the x-ray source 14 and the object 304 relative to the coordinate system fixed with respect to the object 304. At Step 808, the image reconstructor 34 employs a function that describes the times the interpreted movement of the x-ray source 14 goes around a point of the object 304. At Step 810, the image reconstructor 34 reconstructs a CT image of the object 304.

An exemplary reconstruction formula is linked to the turn number function N in evaluating the trajectory 402 of the x-ray source 14 in the curve C for reconstructing the image of the points on the target object 304. Every point in the reconstruction plane has a unique value provided by the turn number function N applied to the trajectory 402 of the x-ray source 14 in the curve C. There is a correspondence between the points in the reconstruction plane and the values provided by the turn number function N applied to the trajectory 402 of the x-ray source 14 in the curve C.

The value of a point on the curve C cannot be recovered by the exemplary equation (13), because the turn number function $N(\vec{r})$ is not well defined on the curve C. Nevertheless, the value of such a point can be obtained by the continuity of the test function $\Psi(\vec{r})$. For a point outside the curve C, its value cannot be recovered because $N(\vec{r})=0$, but this does not imply that $\Psi(\vec{r})$ must be zero outside the curve C.

If the curve C is described by two smooth or piecewise smooth functions in exemplary equation (15):

$$D=D(t), \beta=\beta(t), \qquad (15)$$

with $t \in [0, t_0]$, then the exemplary equation (13) can be rewritten as exemplary equation (16):

$$\frac{1}{2}\int_0^{t_0}\int_{-\pi}^{\pi} R(\beta,\gamma_0)h(L\sin(\gamma-\gamma_0)(D\cos\gamma_0\beta'(t)-\sin\gamma_0 D'(t))d\gamma_0 dt = \qquad (16)$$
$$N(\vec{r})\Psi(\vec{r}).$$

If the curve C is described by a smooth or piecewise smooth function $D=D(\beta)$ with $\beta \in [0, 2n\pi]$, then the exemplary equation (13) becomes exemplary equation (17):

$$\frac{1}{2}\int_0^{2n\pi}\int_{-\pi}^{\pi} R(\beta,\gamma_0)h(L\sin(\gamma-\gamma_0))(D\cos\gamma_0-\sin\gamma_0 D'(\beta))d\gamma_0 d\beta = \qquad (17)$$
$$N(\vec{r})\Psi(\vec{r}).$$

Setting n=1 provides exemplary equation (18):

$$\frac{1}{2}\int_0^{2\pi}\int_{-\pi}^{\pi} R(\beta,\gamma_0)h(L\sin(\gamma-\gamma_0))(D\cos\gamma_0-\sin\gamma_0 D'(\beta))d\gamma_0 d\beta = \qquad (18)$$
$$N(\vec{r})\Psi(\vec{r}).$$

It may be noted that exemplary equation (18) does not require an absolute operation, as will be appreciated by those skilled in the art.

In the circular scanning case, $D(\beta)=D_0=$constant, and in exemplary equation (19):

$$\frac{1}{2}\int_0^{2\pi}\int_{-\pi}^{\pi} R(\beta,\gamma_0)h(L\sin(\gamma-\gamma_0))D_0\cos\gamma_0 d\gamma_0 dB = \begin{cases} \Psi(\vec{r}), & |\vec{r}|<D_0. \\ 0, & |\vec{r}|>D_0. \end{cases} \qquad (19)$$

If the function to be recovered is zero outside the scanning circle, then the exemplary equation (19) becomes the well-known fan-beam reconstruction formula of exemplary equation (20):

$$\frac{1}{2}\int_0^{2\pi}\int_{-\pi/2}^{\pi/2} R(\beta,\gamma_0)h(L\sin(\gamma-\gamma_0))D_0\cos\gamma_0\,d\gamma_0\,d\beta = \Psi(\vec{r}). \quad (20)$$

Now is presented an illustrative discussion of exemplary application in CT imaging for moving objects, for explanatory purposes.

Figure 9:
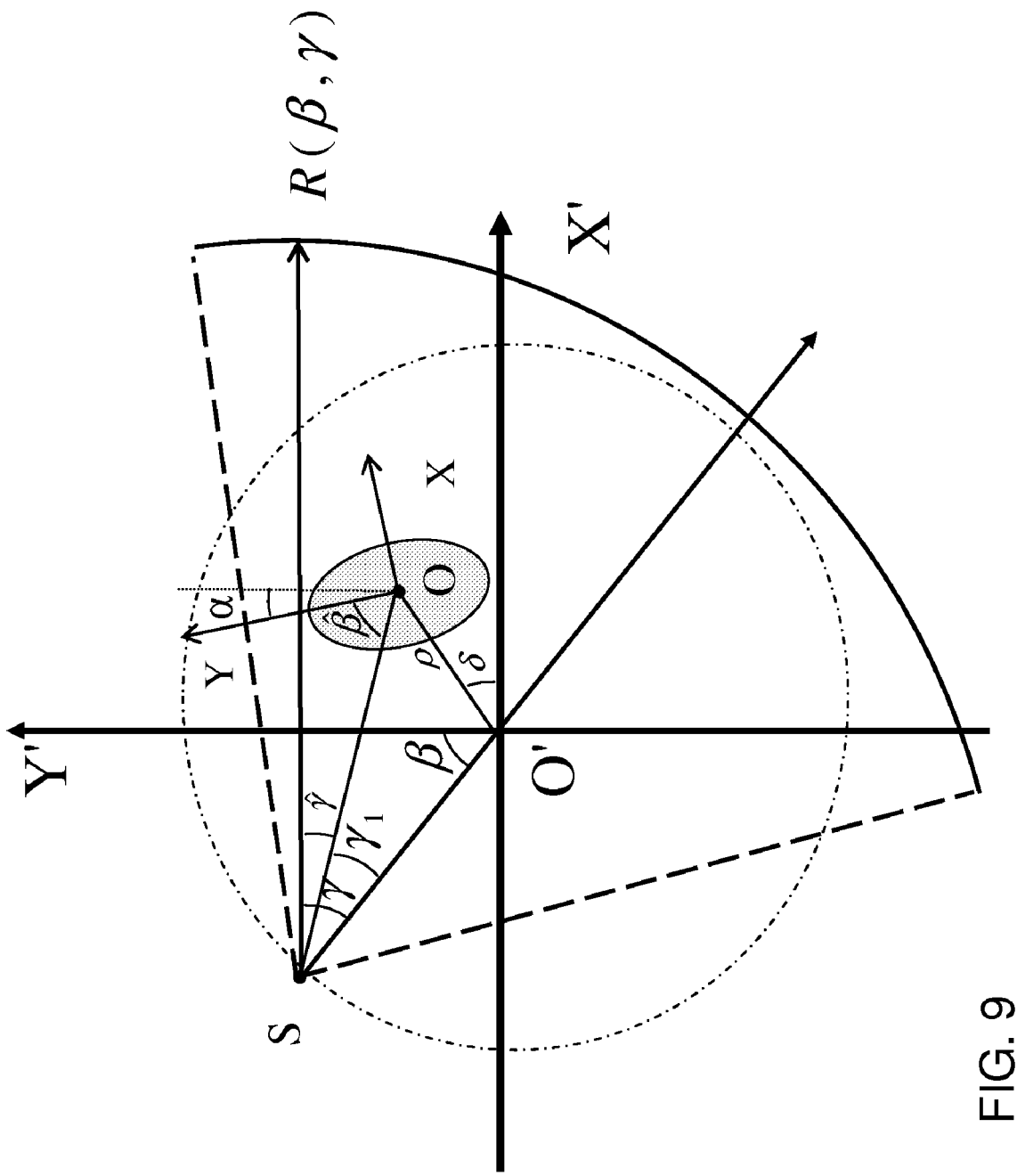
FIG. 9 illustrates a coordinate system based on a scanner as well as a coordinate system based on an object to be scanned.

Referring to FIG. 9, a scanner coordinate system based on the gantry 12 is represented as O'X'Y' and a coordinate system OXY is based on the target object 304. The coordinate system OXY in an example is fixed to the target object 304. In the scanner coordinate system O'X'Y', the motion of the x-ray source 14 is a uniform circular motion described by exemplary equation (21):

$$D(t) = D_0 = \text{constant},\ \beta(t) = \frac{2\pi}{T}t, \quad (21)$$

where $D_0$ denotes the distance between the x-ray source 14 and T the scanning period, such as one second. The data acquisition system (DAS) 32 records projection data $R(\beta,\gamma)$ for every view angle $\beta$ and every ray angle $\gamma$. In the case of a target object 304 that is steady, for example, a still head of the patient 22, one can employ exemplary equation (20) to reconstruct the target object 304.

In the case of motion of the target object 304, for example, a moving head of the patient 22, one employs (x', y') and α to represent the center O and orientation of the target object 304, respectively. One can describe the motion of the target object 304 with the exemplary equations (22) and (23):

$$x'=x'(t),\ y'=y'(t),\ \alpha=\alpha(t), \quad (22)$$

or $$\rho=\rho(t),\ \delta=\delta(t),\ \alpha=\alpha(t), \quad (23)$$

where (ρ,δ) are the polar coordinates of the center of the target object 304 one obtains exemplary equation (24):

$$x=\rho\cos\delta,\ y=\rho\sin\delta. \quad (24)$$

In the coordinate system OXY based on the target object 304, the motion of the x-ray source 14 can be described by exemplary equations (25) and (26):

$$\hat{D}(t) = \sqrt{D_0^2 + \rho^2(t) + 2D_0\rho(t)\sin(\beta(t)-\delta(t))}, \quad (25)$$

$$\hat{\beta}(t)=\beta(t)+\gamma_1(t)-\alpha(t), \quad (26)$$

where one has exemplary equation (27):

$$LOSO' = \gamma_1(t) = tg^{-1}\frac{\rho(t)\cos(\beta(t)-\delta(t))}{D_0+\rho(t)\sin(\beta(t)-\delta(t))}. \quad (27)$$

The projection data can be expressed as exemplary equation (28):

$$\hat{P}(\hat{\beta},\hat{\gamma})=P(\beta,\gamma)=P(\hat{\beta}-\gamma_1+\alpha,\hat{\gamma}+\gamma_1). \quad (28)$$

The image reconstructor 34 in an example employs exemplary equation (13) to reconstruct the image of the target object 304 in the coordinate system OXY based on the target object 304. It may be noted that the loci described by exemplary equation (25) or (26) are relatively general.

Figure 10:
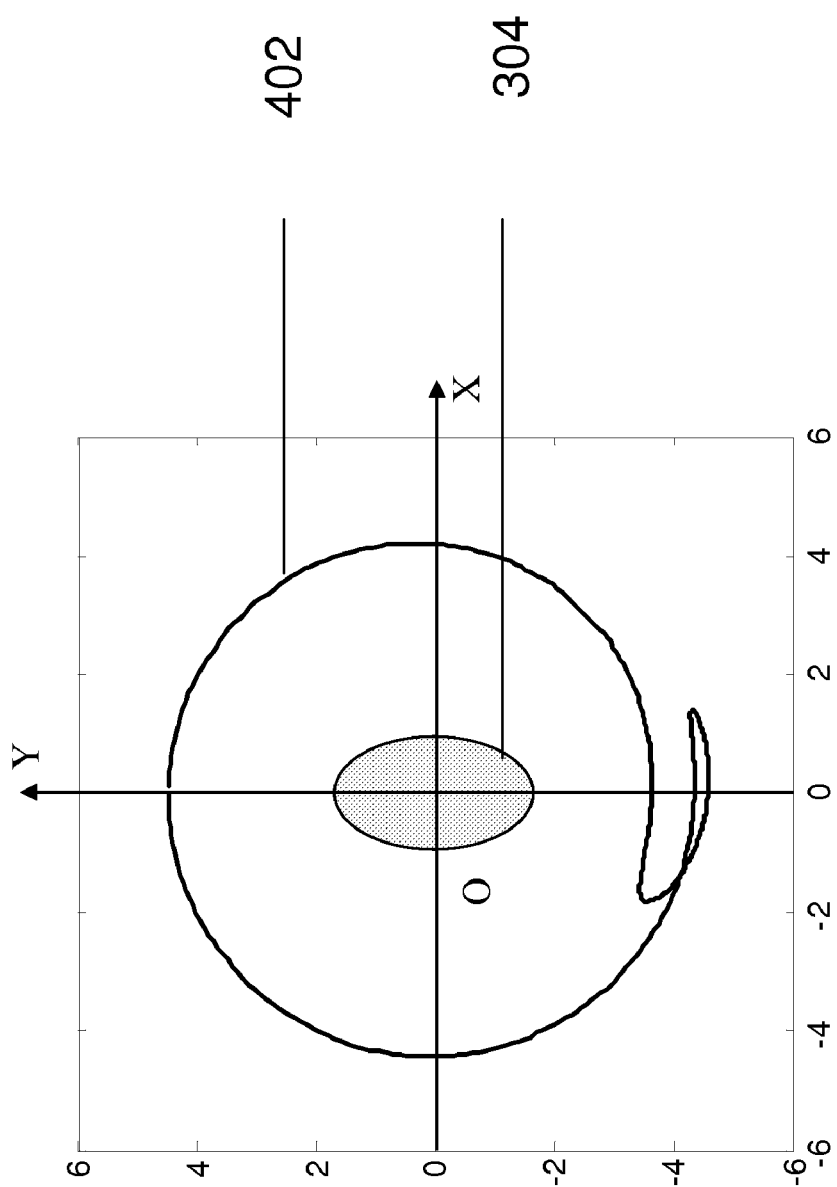
FIG. 10 illustrates a compound nature of a trajectory of a high frequency electromagnetic energy projection source in a coordinate system based on an object.

For illustrative purposes, one may consider an example of a trajectory 402 of the x-ray source 14 made of only one circle (360°). The target object 304 may move during the scan according to exemplary equations (29):

$$x'(t) = \frac{1}{2}\sin\left(\frac{\pi}{T}t\right), \quad (29)$$

$$y'(t) = -\frac{1}{2}\cos\left(\frac{2\pi}{T}t\right),$$

$$\alpha(t) = -\frac{\pi}{2}\sin\left(\frac{2\pi}{T}t\right),$$

where t∈[0,T]. FIG. 10 illustrates the compound trajectory 402 of the x-ray source 14 in the coordinate system OXY based on the target object 304. Clearly, this curve does not satisfy the conditions needed for an exemplary previous approach to be able to reconstruct a quality image of the target object 304.

Figures 11, 12:
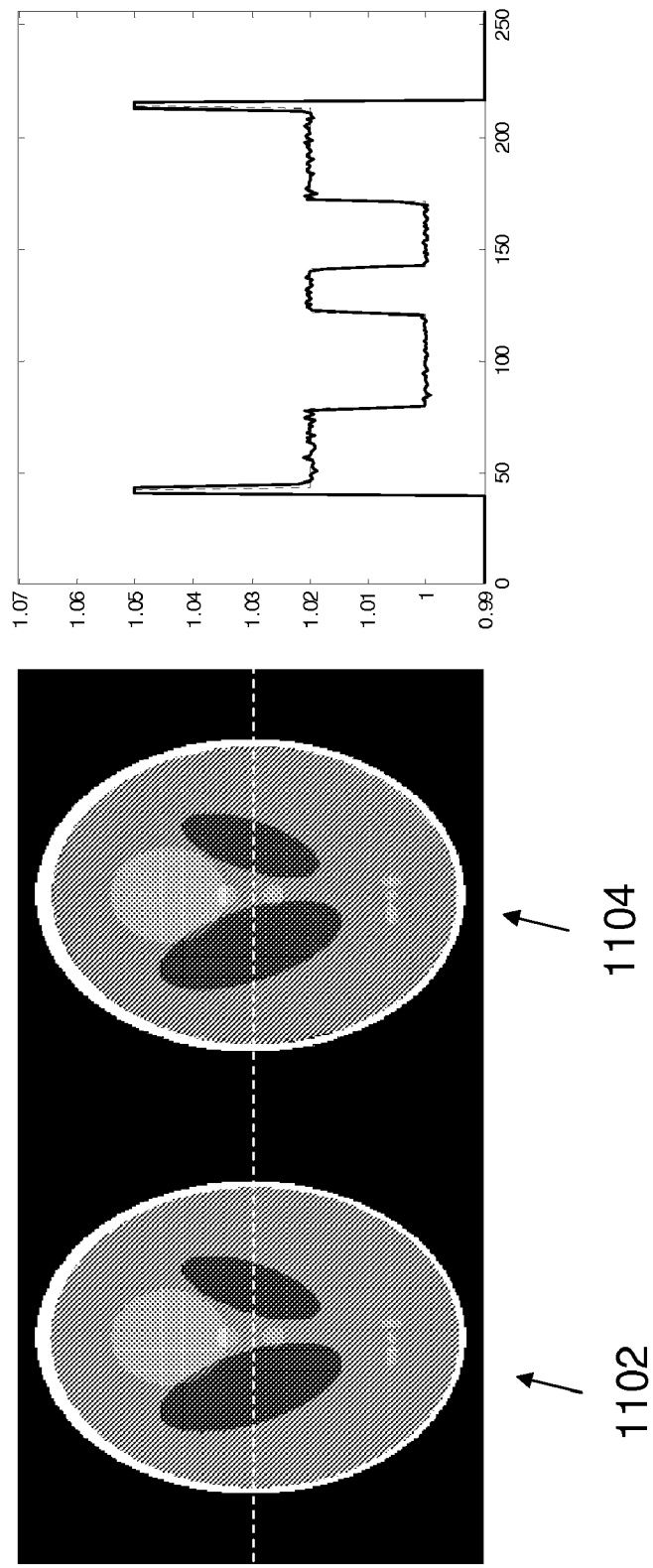
FIG. 11 represents an exemplary ideal image of an object and an exemplary reconstructed image of the object.
FIG. 12 represents the profile of the horizontal midline of the ideal images and reconstructed images of the Shepp-Logan Phantom.

As will be appreciated by those skilled in the art, Shepp-Logan phantom is employed to simulate the target object 304, for example, the head of the patient 22, and exemplary equation (13) is employed to reconstruct the image of the target object 304. FIG. 11 represents an exemplary ideal image 1102 and an exemplary reconstructed image 1104 of the Shepp-Logan phantom. FIG. 12 represents the profile of the horizontal midline of the ideal images and reconstructed images of the Shepp-Logan Phantom. FIG. 12 plots the profiles along the horizontal midline of Shepp-Logan for both the exemplary ideal image 1102 and the exemplary reconstructed image 1104. The exemplary reconstructed image 1104 was compared to the ground truth with an error 0.37% defined by exemplary equation (30):

$$\text{error} = \sqrt{\sum_{i=1}^{N}\sum_{j=1}^{N}(x'_{i,j}-x_{i,j})^2 \Big/ \sum_{i=1}^{N}\sum_{j=1}^{N}x_{i,j}^2} \quad (30)$$

where N=256, and $x_{i,j}$ and $x'_{i,j}$ are the original and computed pixel values, respectively. The parameters used were $D_0=4$, the number of views 512, and the detectors 20 in the detector array 18 numbered 2048 and were uniformly distributed along a half circle. The image size was set to 2*2 and discretized into a matrix of 256*256 pixels. The display window was set to [0.99, 1.05].

Figure 13:
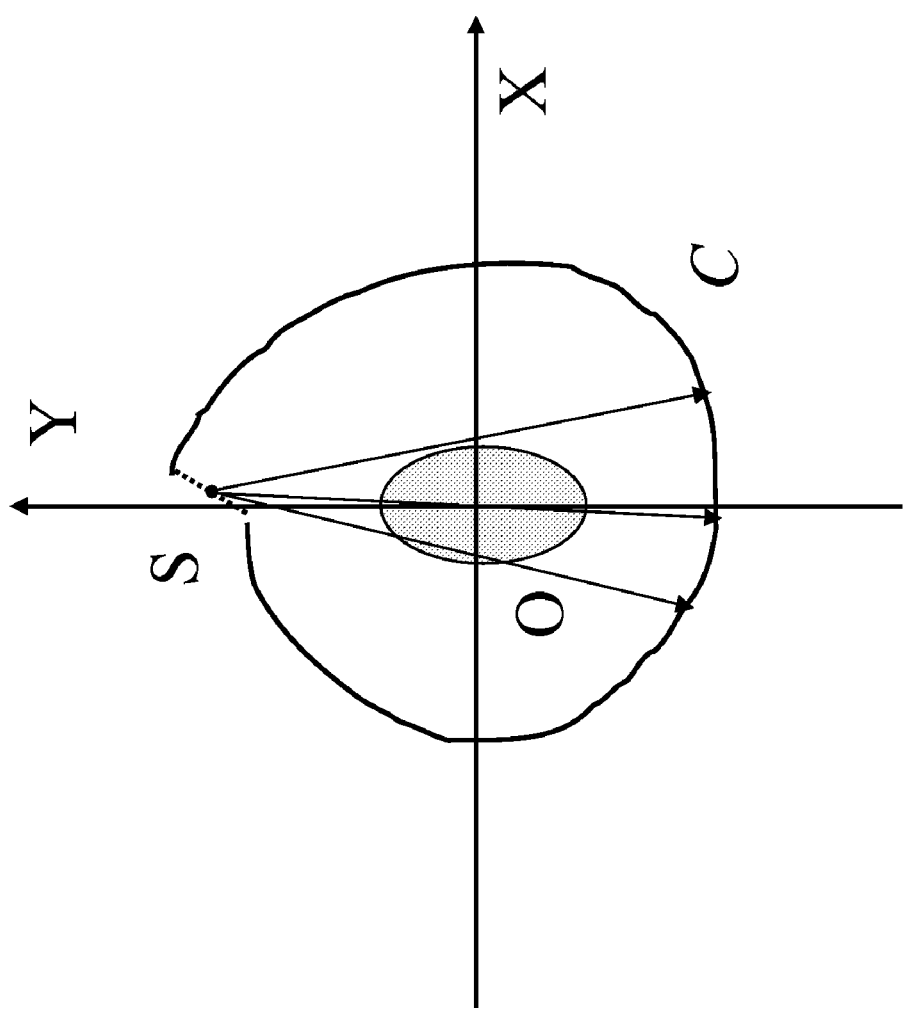
FIG. 13 represents an open source locus closed by a virtual path.

FIG. 13 represents an open source locus closed by a virtual path. In an example, the required projection data on the virtual path can be obtained from the measured projection data. In an exemplary implementation, the scanning locus is not necessarily closed in the coordinate system OXY based on the target object 304. In this case, one can close the locus by adding a virtual path. The projection data at the virtual path can be obtained by interpolation from the measured projection data. Alternatively, the traditional half-scan weighting scheme can also be applied to the exemplary formulation framework. Therefore, the exemplary formulation provides a general fan-beam reconstruction for arbitrary locus.

Presented herein is a new fan-beam reconstruction formula in the case of general scanning loci. An exemplary implementation provides a simple and effective method for fan beam reconstruction along a general locus. The locus needs to be continuous rather than differentiable. The well-known Ram-Lak filter is used in the reconstruction so the filtering process in this fan-beam reconstruction formula in an example is easy to implement, for example, in one or more of the computer, 36, the DAS 32 and/or the image reconstructor 34.

An implementation encompasses a scheme for CT imaging with a complicated scanning trajectory. In an exemplary scheme, projection data are filtered by the Ram-Lak filter or its variant, multiplied by increments relative to the view angle and the focus distance, and backprojected to form an image with help of the turn number function. Exemplary features of the scheme comprise (1) use of the turn number function, (2) the locus not necessarily being differentiable, and (3) removal of the traditional assumption that the object function should be zero outside of the field of view.

Additional exemplary features comprise use of the turn number function in making easier the CT image reconstruction of objects with a complicated locus and an ability to handle small local loops and zigzags. An implementation encompasses a method for CT imaging of objects with a known motion, where the real motion of the object is interpreted as a complicated locus in the object oriented coordinate system, and compensated using the new reconstruction formula.

Figure 14:
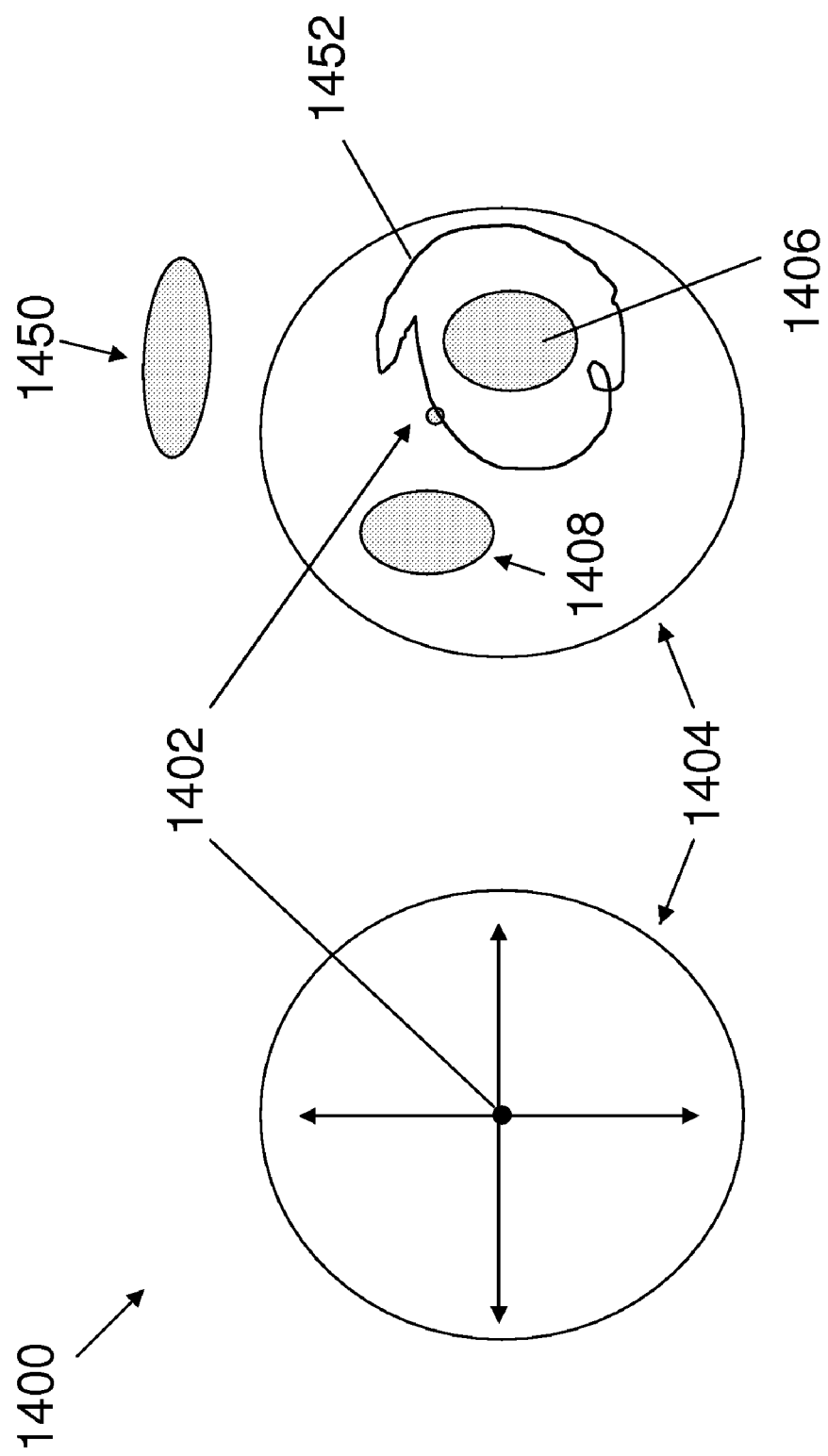
FIG. 14 represents a CT system for on-line measurement of a part of a large machine.

FIG. 14 represents a CT system for on-line measurement of a part of a large machine. Exemplary detector system 1400, made of a radioactive source 1402 and a circular detector 1404, is designed for on-line measurement of a large machine in industry. The γ rays emitted from the radioactive source 1402 pass through the measured part 1406 and arrive at the detector 1404. The detector 1404 and unmeasured parts 1408 and 1450 of the machine may be connected in the three dimensional space and it may not be easy to divide them. Typically, the radioactive source 1402 is small so it can move along a flexible planar curve 1452 in the spare space of the large machine. The detector 1404 can either move with the radioactive source 1402 or be fixed in the space, depending on the spare space of the machine. The existence of the neighboring parts 1408 and 1450 does not have influence on the imaging system. If the measured part 1406 has a known motion such as a vibration, the reconstruction can be done in the coordinate system fixed on the part 1406, as described above. The system also works for underwater objects such as the support of a bridge, because the water does not have influence on the imaging system according our formula. To set up the detector system 1400 easily, the detector 1404 may be a circle made of two parts connected by a joint.

A CT system comprises a radioactive source for probing one or more parts of a large object. The radioactive source moves along a complicated trajectory in the spare space of the large object. An exemplary method serves to deal with an open source locus. The open locus is closed by virtual paths and the projection data from the virtual locus are obtained from the measured data via interpolation, and processed using the new reconstruction formula.

An implementation of the system 10 and/or 1400 in an example comprises a plurality of components such as one or more of electronic components, hardware components, and/or computer software components. A number of such components can be combined or divided in an implementation of the system 10 and/or 1400. An exemplary component of an implementation of the system 10 and/or 1400 employs and/or comprises a set and/or series of computer instructions written in or implemented with any of a number of programming languages, as will be appreciated by those skilled in the art. An implementation of the system 10 and/or 1400 in an example comprises any (e.g., horizontal, oblique, or vertical) orientation, with the description and figures herein illustrating an exemplary orientation of an implementation of the system 10 and/or 1400, for explanatory purposes.

An implementation of the system 10 and/or the system 1400 encompasses an article. The article comprises one or more computer-readable signal-bearing media. The article includes means in the one or more media for interpreting relative movement between a high frequency electromagnetic energy projection source and a target object as interpreted movement of the high frequency electromagnetic energy projection source relative to a coordinate system fixed with respect to the target object for an interpretation of CT image data of the target object. The article includes means in the one or more media for reconstructing a CT image of the target object through employment of a function that describes how many times the interpreted movement of the high frequency electromagnetic energy projection source goes around a particular point of the target object.

An implementation of the system 10 and/or the system 1400 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the system 10 and/or the system 1400 comprises the recordable data storage medium of the image reconstructor 34, and/or the mass storage device 38 of the computer 36. A computer-readable signal-bearing medium for an implementation of the system 10 and/or the system 1400 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1400, for instance, one or more of a telephone network, a local area network ("LAN"), a wide area network ("WAN"), the Internet, and/or a wireless network.

The steps or operations described herein are examples. There may be variations to these steps or operations without departing from the spirit of the invention. For example, the steps may be performed in a differing order, or steps may be added, deleted, or modified.

The present invention has been described in terms of the preferred embodiment, and it is recognized that equivalents, alternatives, and modifications, aside from those expressly stated, are possible and within the scope of the appending claims.

What is claimed is:

1. A CT system, comprising:
   an x-ray source that emits a beam of x-rays toward an object to be imaged;
   a detector that receives x-rays emitted by the x-ray source;
   a data acquisition system (DAS) operably connected to the detector; and
   a computer operably connected to the DAS and programmed to:

reconstruct a CT image of the object to comprise a plurality of CT images, of a respective plurality of points of the object, through employment of a function that describes how many times a trajectory curve, of an interpretation of relative movement between the x-ray source and the object as that of the x-ray source, goes around each of the plurality of points of the object.

2. The CT system of claim 1, wherein the computer operably connected to the DAS is programmed to:
prepare the interpretation of the relative movement between the x-ray source and the object as that of the x-ray source as the trajectory curve;
prepare the trajectory curve as interpreted movement of the x-ray source relative to a coordinate system fixed with respect to the object; and
reconstruct the CT image of the object through employment of the function, wherein the function comprises a turn function that describes how many times the trajectory curve loops around a particular point, of the plurality points of the object, in a predefined direction.

3. The CT system of claim 1, wherein the computer operably connected to the DAS is programmed to:
prepare the interpretation of the relative movement between the x-ray source and the object as that of the x-ray source as the trajectory curve;
prepare the trajectory curve as interpreted movement of the x-ray source relative to a coordinate system fixed with respect to the object; and
reconstruct the CT image of the object through employment of the function, wherein the function looks outward from a particular point, of the plurality points of the object, and counts in the trajectory curve:
a number of turns in a predefined direction about the particular point of the object; and
a number of turns opposite to the predefined direction about the particular point of the object.

4. The CT system of claim 1, wherein the computer operably connected to the DAS is programmed to:
prepare the interpretation of the relative movement between the x-ray source and the object as that of the x-ray source as the trajectory curve;
prepare the trajectory curve as interpreted movement of the x-ray source relative to a coordinate system fixed with respect to the object; and
reconstruct the CT image of the object through employment of the function, wherein the function yields a net number of times that the trajectory curve of the x-ray source goes around a particular point, of the plurality points of the object, in a predefined direction.

5. The CT system of claim 4, wherein the computer operably connected to the DAS is programmed to reconstruct the CT image of the object through employment of the function, wherein the function treats:
a component value of the trajectory curve in the predefined direction; and
a component value of the trajectory curve opposite to the predefined direction;
to comprise a tendency to cancel each other out.

6. The CT system of claim 1, wherein the computer operably connected to the DAS is programmed to:
prepare the interpretation of the relative movement between the x-ray source and the object as that of the x-ray source as the trajectory curve;
prepare the trajectory curve as interpreted movement of the x-ray source relative to a coordinate system fixed with respect to the object; and
reconstruct the CT image of the object through employment of the function, wherein the function identifies a point of the object that is to be omitted from the plurality of CT images of the respective plurality of points of the object because of a condition of the point of the object as tested by the function.

7. The CT system of claim 1, wherein the computer operably connected to the DAS is programmed to:
prepare the interpretation of the relative movement between the x-ray source and the object as that of the x-ray source as the trajectory curve;
prepare the trajectory curve as interpreted movement of the x-ray source relative to a coordinate system fixed with respect to the object; and
reconstruct the CT image of the object through employment of the function, wherein the function provides respective distinct values for the plurality of points of the object in a reconstruction plane that comprises the coordinate system fixed with respect to the object.

8. The CT system of claim 1, wherein the computer operably connected to the DAS is programmed to:
prepare the interpretation of the relative movement between the x-ray source and the object as that of the x-ray source as the trajectory curve;
prepare the trajectory curve as interpreted movement of the x-ray source relative to a coordinate system fixed with respect to the object; and
reconstruct the CT image of the object through employment of the function, wherein the function provides a correspondence between values returned by the function and the plurality of points on the object in a reconstruction plane that comprises the coordinate system fixed with respect to the object.

9. The CT system of claim 1, wherein the object comprises one or more parts of a large object, wherein the computer operably connected to the DAS is programmed to:
move a radioactive source along a complicated trajectory in a spare space of a large object for probing the one or more parts of the large object;
employ one or more virtual paths to close an open source locus to create a virtual locus as the trajectory curve; and
obtain projection data at the virtual locus from measured data via interpolation.

10. A method, comprising the steps of:
interpreting relative movement between a high frequency electromagnetic energy projection source and a target object as interpreted movement of the high frequency electromagnetic energy projection source relative to a coordinate system fixed with respect to the target object for an interpretation of CT image data of the target object; and
reconstructing a CT image of the target object through employment of a function that describes how many times the interpreted movement of the high frequency electromagnetic energy projection source goes around a particular point of the target object.

11. The method of claim 10, wherein the step of interpreting the relative movement between the high frequency electromagnetic energy projection source and the target object as the interpreted movement of the high frequency electromagnetic energy projection source relative to the coordinate system fixed with respect to the target object for the interpretation of the CT image data of the target object comprises the step of:
interpreting actual movement of the target object as at least part of the interpreted movement of the high frequency electromagnetic energy projection source relative to the coordinate system fixed with respect to the target object for the interpretation of the CT image data of the target object.

12. The method of claim 10, wherein the step of interpreting the relative movement between the high frequency electromagnetic energy projection source and the target object as the interpreted movement of the high frequency electromagnetic energy projection source relative to the coordinate system fixed with respect to the target object for the interpretation of the CT image data of the target object comprises the step of:

interpreting actual movement of the high frequency electromagnetic energy projection source as at least part of the interpreted movement of the high frequency electromagnetic energy projection source relative to the coordinate system fixed with respect to the target object for the interpretation of the CT image data of the target object.

13. The method of claim 10, wherein the step of interpreting the relative movement between the high frequency electromagnetic energy projection source and the target object as the interpreted movement of the high frequency electromagnetic energy projection source relative to the coordinate system fixed with respect to the target object for the interpretation of the CT image data of the target object comprises the step of:

interpreting complex movement of the target object as at least part of the interpreted movement of the high frequency electromagnetic energy projection source relative to the coordinate system fixed with respect to the target object for the interpretation of the CT image data of the target object.

14. The method of claim 10, wherein the step of interpreting the relative movement between the high frequency electromagnetic energy projection source and the target object as the interpreted movement of the high frequency electromagnetic energy projection source relative to the coordinate system fixed with respect to the target object for the interpretation of the CT image data of the target object comprises the step of:

interpreting complex movement of the high frequency electromagnetic energy projection source as at least part of the interpreted movement of the high frequency electromagnetic energy projection source relative to the coordinate system fixed with respect to the target object for the interpretation of the CT image data of the target object.

15. The method of claim 10, wherein the step of reconstructing the CT image of the target object through employment of the function that describes how many times the interpreted movement of the high frequency electromagnetic energy projection source goes around the particular point of the target object comprises the step of:

employing the interpreted movement of the high frequency electromagnetic energy projection source as non-circular movement of the high frequency electromagnetic energy projection source relative to an origin of the coordinate system fixed with respect to the target object.

16. The method of claim 10, wherein the step of reconstructing the CT image of the target object through employment of the function that describes how many times the interpreted movement of the high frequency electromagnetic energy projection source goes around the particular point of the target object comprises the step of:

employing the interpreted movement of the high frequency electromagnetic energy projection source as a source trajectory with changes in radius and direction of the high frequency electromagnetic energy projection source relative to an origin of the coordinate system fixed with respect to the target object.

17. The method of claim 10, wherein the step of reconstructing the CT image of the target object through employment of the function that describes how many times the interpreted movement of the high frequency electromagnetic energy projection source goes around the particular point of the target object comprises the steps of:

employing the interpreted movement of the high frequency electromagnetic energy projection source as a source trajectory that in some places loops around and in some places goes back and forth in the coordinate system fixed with respect to the target object;

allowing the source trajectory to not necessarily be differentiable; and operating without an assumption the function should be zero outside a field of view of the target object.

18. A method for CT imaging with a complicated scanning trajectory, the method comprising the steps of:

filtering projection data by Ram-Lak filter or a variant of the Ram-Lak filter, wherein the projection data correspond to the complicated scanning trajectory;

multiplying the projection data by increments relative to a view angle and focus distance; and backprojecting the projection data to form an image through employment of a turn number function.

19. The method of claim 18, further comprising the step of:

handling the complicated scanning trajectory with small local loops and/or zigzags.

20. The method of claim 18, wherein the step of filtering projection data by the Ram-Lak filter or the variant of the Ram-Lak filter comprises the step of:

interpreting a known real motion of an object as the complicated scanning trajectory in a coordinate system oriented with respect to the object.

* * * * *